United States Patent [19]

Gates et al.

[11] 4,056,625
[45] Nov. 1, 1977

[54] PESTICIDAL COMPOSITIONS CONTAINING BENZODIOXOLE DERIVATIVES AND METHODS OF COMBATTING PESTS

[75] Inventors: Peter Stuart Gates, Cambridge; John Gillon, Linton, both of England

[73] Assignee: Fisons Limited, London, England

[21] Appl. No.: 641,925

[22] Filed: Dec. 18, 1975

Related U.S. Application Data

[60] Division of Ser. No. 389,202, Aug. 17, 1973, Pat. No. 3,948,952, which is a continuation-in-part of Ser. No. 347,462, Jan. 29, 1973, abandoned, which is a continuation-in-part of Ser. No. 130,487, April 1, 1971, Pat. No. 3,736,338, which is a continuation-in-part of Ser. No. 706,628, Feb. 19, 1968, abandoned.

[30] Foreign Application Priority Data

Aug. 22, 1972 United Kingdom ............... 39001/72
Dec. 6, 1972 United Kingdom ............... 56170/72

[51] Int. Cl.$^2$ ..................... A01N 9/28; C07D 317/46
[52] U.S. Cl. ............................. 424/282; 260/340.5 R
[58] Field of Search ..................... 424/282; 260/340.5

[56] References Cited

U.S. PATENT DOCUMENTS

| | | |
|---|---|---|
| 2,856,411 | 10/1958 | Prill ................................... 424/282 |
| 3,338,783 | 8/1967 | Popjak ............................... 424/282 |
| 3,682,973 | 8/1972 | Eriksoo et al. .................... 260/340.5 |

*Primary Examiner*—V. B. Turner
*Attorney, Agent, or Firm*—Wenderoth, Lind & Ponack

[57] ABSTRACT

Substituted benzodioxoles of the formula:

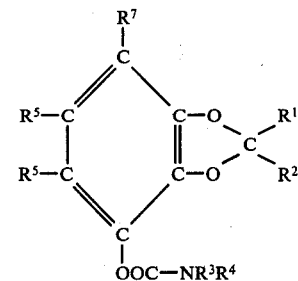

wherein
$R^1$ and $R^2$ are hydrogen or alkyl of 1 to 6 carbon atoms or together with the linking carbon atom form a cycloalkane or cycloalkene ring of 5 to 7 carbon atoms;
$R^3$ is hydrogen, alkyl of 1 to 4 carbon atoms or acyl;
$R^4$ is alkyl of up to 4 carbon atoms, alkenyl of up to 4 carbon atoms or alkynyl of up to 4 carbon atoms; and
$R^5$, $R^6$ and $R^7$ are hydrogen, halogen or alkyl of 1 to 4 carbon atoms
are valuable pesticides, particularly insecticides.

33 Claims, No Drawings

PESTICIDAL COMPOSITIONS CONTAINING BENZODIOXOLE DERIVATIVES AND METHODS OF COMBATING PESTS

CROSS-REFERENCE TO RELATED APPLICATIONS

This is a division of application Ser. No. 389,202, filed Aug. 17, 1973, now U.S. Pat. No. 3,948,952, which application is a continuation-in-part of application Ser. No. 327,462, filed Jan. 29, 1973, now abandoned, which is further a continuation-in-part of application Ser. No. 130,487, filed Apr. 1, 1971, now U.S. Pat. No. 3,736,338, which in turn is a continuation-in-part of application Ser. No. 706,628, filed Feb. 19, 1968 now abandoned.

The present invention relates to certain substituted benzodioxoles which have been found to possess pesticidal activity, to their preparation and to pesticidal compositions containing the same.

Accordingly the present invention is for the substituted benzodioxoles of the formula:

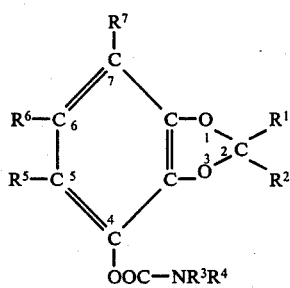

wherein $R^1$ and $R^2$ are selected from hydrogen and alkyl (for example of 1–6 carbon atoms, such as methyl, ethyl or butyl) substituted or unsubstituted, or $R^1$ and $R^2$ together with the linking carbon atom form a cycloalkane or cycloalkene ring of 5 to 7 carbon atoms, and wherein $R^3$ is selected from hydrogen, alkyl (for example of 1–4 carbon atoms, such as methyl or ethyl) substituted or unsubstituted and acyl (for example lower alkanoyl e.g. acetyl or propionyl, or benzoyl) and where $R^4$ is selected from alkyl (for example of 1–4 carbon atoms such as methyl or ethyl), alkenyl (for example of 1–4 carbon atoms such as allyl) and alkynyl (for example of 1–4 carbon atoms such as propargyl), and $R^5$, $R^6$ and $R^7$ are selected from hydrogen, halogen (for example chlorine, bromine, iodine or fluorine) and alkyl (for example of 1–4 carbon atoms such as methyl or ethyl) substituted or unsubstituted.

According to a preferred embodiment of the invention $R^1$ and $R^2$ are selected from hydrogen and alkyl or together with the linking carbon atom form a cycloalkane ring of 5 or 6 carbon atoms, $R^3$ is selected from hydrogen, alkyl and acyl, $R^4$ is selected from alkyl, alkenyl and alkynyl, and $R^5$, $R^6$ and $R^7$ are selected from hydrogen and alkyl.

The present invention is also for pesticidal compositions which contain as an active ingredient a substituted benzodioxole as identified above. The pesticidal composition suitably also contains at least one material selected from the group comprising carriers, wetting agents, inert diluents and solvents.

The present invention is also for the treatment of plants, animals, the soil, materials or areas, which comprises applying thereon or thereto a substituted benzodioxole as identified above.

The present invention is also for the preparation of the substituted benzodioxoles as identified above which comprises reacting a 4-hydroxyl-1,3-benzodioxole with an isocyanate of the formula $R^4NCO$ ($R^3$ in the product thus being hydrogen) or a substituted carbamyl chloride of the formula $R^3R^4NCOCl$ (except where $R^3$ is acyl); in the case of substituted benzodioxoles where $R^3$ is acyl, these may be prepared by acylating the corresponding compound where $R^3$ is hydrogen. The substituted benzodioxoles may also be prepared by reacting a 1,3-benzodioxolyl-4-chloroformate (which may be prepared by reacting a 4-hydroxyl-1,3-benzodioxole with phosgene) with an amine or amide of the formula $R^3R^4NH$. The groups $R^3$ and $R^4$ have the significance indicated above.

According to a preferred embodiment of the invention the substituted benzodioxole is a compound of the formula above where $R^5$, $R^6$ and $R^7$ are selected from hydrogen and alkyl, especially where $R^1$ and $R^2$ are methyl groups.

In the present compounds, it is preferred that $R^1$ and $R^2$ are selected from the group consisting of hydrogen and alkyl of 1 to 6 carbon atoms and a group where $R^1$ and $R^2$ together with the linking carbon atom form a cycloalkane ring of 5 to 7 carbon atoms, and that $R^3$ is selected from the group consisting of hydrogen, alkyl of 1 to 4 carbon atoms and lower alkanoyl (or alkanoyl of 2 to 5 carbon atoms) (especially that $R^3$ is selected from the group consisting of hydrogen, alkyl of 1 to 4 carbon atoms, acetyl and propionyl, for example hydrogen, alkyl of 1 to 4 carbon atoms and acetyl).

It is especially preferred that $R^1$ and $R^2$ each represent a methyl group.

It is also preferred that $R^3$ represents a hydrogen atom and $R^4$ represents a methyl group.

Preferably also, one of $R^5$, $R^6$ and $R^7$ is selected from the group consisting of hydrogen, halogen and alkyl of 1 to 4 carbon atoms and the others of $R^5$, $R^6$ and $R^7$ each represent a hydrogen atom, and it is especially preferred that each of $R^5$, $R^6$ and $R^7$ represents a hydrogen atom.

Thus, a preferred group of compounds are of the formula above wherein $R^1$ and $R^2$ are selected from the group consisting of hydrogen and alkyl of 1 to 6 carbon atoms and a group where $R^1$ and $R^2$ together with the linking carbon atom form a cycloalkane ring of 5 to 7 carbon atoms;

$R^3$ is selected from the group consisting of hydrogen, alkyl of 1 to 4 carbon atoms and lower alkanoyl (e.g. acetyl);

$R^4$ is selected from the group consisting of alkyl of up to 4 carbon atoms, alkenyl of up to 4 carbon atoms and alkynyl of up to 4 carbon atoms; and one of $R^5$, $R^6$ and $R^7$ is selected from the group consisting of hydrogen, halogen and alkyl of 1 to 4 carbon atoms; and the others of $R^5$, $R^6$ and $R^7$ each represent a hydrogen atom.

Particularly preferred compounds are 1,3-benzodioxol-4-yl N-acetyl-N-methylcarbamate (compound 1), 2,2-dimethyl-1,3-benzodioxol-4-yl N-propionyl-N-methylcarbamate (compound 2), 2,2-dimethyl-1,3-benzodioxol-4-yl N-butyryl-N-methylcarbamate (compound 3), 2,2-dimethyl-1,3-benzodioxol-4-yl N-pentanoyl-N-methylcarbamate (compound 4), 2,2-dimethyl-1,3-benzodioxol-4-yl N-methylcarbamate (compound 5) and 2,2,7-trimethyl-1,3-benzodioxol-4-yl N-methylcarbamate Features of the present compounds are illustrated in the Examples. Compound 5 is outstanding.

Compounds 1, 2, 3 and 4 are also outstanding. They possess outstandingly good combinations of activity, persistency and lack of mammalian toxicity. They have lower mammalian toxicity than does compound 5; this is especially so for compounds 1 and 3. Compounds 2 and 4 are preferred to compounds 1 and 3, however, because compounds 2 and 4 have shown outstandingly good activity against cockroaches, like compound 5; this is surprising since 2,2-dimethyl-1,3-benzodioxol-4-yl N-acetyl-N-methylcarbamate (compound 6) shows low activity against cockroaches. Furthermore, compounds 2 and 4 have much better persistency on sheep against sheep maggot fly (*Lucila sericata*), of the order Diptera, than compound 5. Compounds 1, 2, 3 and 4 also show as good or better activity against houseflies than does compound 5, which is surprising since compound 6 is worse. In addition, compounds 2 and 3 are as active as compound 5 against sheep maggot fly although compound 6 is worse. Compounds 1, 2, 3 and 4 are also liquids and are of higher solubility in organic solvents than is compound 5, which is a solid, and hence are easier to make up into the preferred formulations, which are liquid.

The present compounds are pesticides particularly insecticides.

The substituted benzodioxoles are generally water insoluble and may be formulated in any of the ways commonly adopted for insoluble compounds.

If desired the substituted benzodioxoles may be dissolved in a water immiscible solvent, such as for example a high boiling hydrocarbon, suitably containing dissolved emulsifying agents so as to act as a self-emulsifiable oil on addition to water.

The substituted benzodioxoles may also be admixed with a wetting agent with or without an inert diluent to form a wettable powder which is soluble or dispersable in water, or may be mixed with the inert diluent to form a solid or powdery product.

Inert diluents with which the substituted benzodioxoles may be incorporated include solid inert media comprising powdered or divided solid materials, for example, clays, sands, talc, mica, fertilizers and the like, such products either comprising dust or larger particle size materials.

The wetting agents used may comprise anionic compounds such as for example soaps, fatty sulphate esters such as dodecyl sodium sulphate, octadecyl sodium sulphate and cetyl sodium sulphate, fatty aromatic sulphonates such as alkylbenzene sulphonates or butyl naphthalene sulphonates, more complex fatty sulphonates such as the amide condensation products of oleic acid and N-methyl taurine or the sodium sulphonate of dioctyl succinate.

The wetting agents may also comprise non-ionic wetting agents such as for example condensation products of fatty acids, fatty alcohols or fatty substituted phenols which ethylene oxide, or fatty esters and ethers of sugars or polyhydric alcohols, or the products obtained from the latter by condensation with ethylene oxide, or the products known as block copolymers of ethylene oxide and propylene oxide. The wetting agents may also comprise cationic agents such as for example cetyl trimethylammonium bromide and the like.

The pesticidal composition may also be in the form of an aerosol composition, suitably using a cosolvent and a wetting agent, in addition to the propellant, which is suitably a polyhalogenated alkane such as dichlorodifluoromethane.

The pesticidal compositions according to the present invention may contain in addition to the substituted benzodioxoles other active insecticides, bactericides and fungicides. It has been found that particular advantages are obtained with mixtures with other insecticides.

The present compounds are active against a wide range of insect and acarid pests, for example vetch aphids (*Megoura viciae*), sheep maggot fly (*Lucilia sericata*) and yellow fever mosquitos (*Aedes aegypti*).

In their various applications the compounds of the invention may be used a various rates. Generally the compounds are applied at a rate of 0.2–12 kg per hectare. For the treatment of plants for the control of pests on plants the compounds are generally applied at a rate of 0.2–10 kg per hectare, usually about 0.25–16 ounces per acre (17–1120 g. per hectare) and preferably 0.5–4 ounces per acre (35–280 g. per hectare). For the treatment of animals (e.g. for the control of ticks), the animal is suitably dipped in or sprayed with a solution containing 30–300 parts per million of the active compound.

In a preferred application, the compounds and especially 2,2-dimethyl-1,3-benzodioxol-4-yl N-methylcarbamate are used to combat domestic and public health insect pests. For this use, the compounds are generally applied indoors, e.g. in buildings or on ships, for example in food preparation or storage areas e.g. in houses, flats, warehouses and ships. The compounds are suitably applied at a rate of 50–2000, preferably about 50–1,000, for example 200, mg per square meter. Thus, applied at this specific rate, suitably as an aqueous spray containing 0.25% active ingredient and prepared by suspending an 80% wettable powder, 2,2-dimethyl-1,3-benzodioxal-4-yl N-methylcarbamate is effective against a wide range of such pests, e.g. ants, bed bugs, fleas, houseflies, silverfish, mosquitoes, wasps, carpet beetles and crickets; it is especially useful against cockroaches.

Compounds 1, 2, 3 and 4 are preferably used against cockroaches or in combating ectoparasites, e.g. fleas, on animals.

The following Examples are given to illustrate the present invention. The parts and percentages are by weight unless otherwise indicated.

EXAMPLE 1

2,2-Dimethyl-4-hydroxy-1,3-benzodioxole (14 parts) in benzene (25 parts) was treated with methyl isocyanate (6 parts) and a few drops of triethylamine with cooling. After standing for 30 minutes, the crystals of 2,2-dimethyl-1,3-benzodioxol-4-yl N-methylcarbamate which formed were filtered off and washed with benzene then with petroleum (boiling point below 40° C.) to yield the pure compound as a white solid, melting point 129°–130° C. (16 parts, 85% yield).

Analysis: Found: C, 59.35; H, 5.90; N, 6.35. $C_{11}H_{13}NO_4$ requires: C, 59.18; H, 5.87; N, 6.28%.

EXAMPLES 2–11

The process of Example 1 was repeated replacing the 2,2-dimethyl-4-hydroxyl-1,3-benzodioxole by the appropriate substituted hydroxy-1,3-benzodioxole to form the following compounds:

2-ethyl-2-methyl-1,3-benzodioxol-4-yl N-methylcarbamate, melting point 86°–87° C.

2,2-tetramethylene-1,3-benzodioxol-4-yl N-methylcarbamate, melting point 123°–124° C.

2,2-pentamethylene-1,3-benzodioxol-4-yl N-methylcarbamate, melting point 90°–91° C.
2-tert-butyl-2-methyl-1,3-benzodioxol-4-yl N-methylcarbamate, melting point 89°–90° C.
2,2,7-trimethyle-1,3-benzodioxol-4-yl N-methylcarbamate, melting point 146°–147° C.
2,2,6-trimethyl-1,3-benzodioxol-4-yl N-methylcarbamate, melting point 136°–138° C.
2-methyl-1,3-benzodioxol-4-yl N-methylcarbamate, melting point 135°–137° C.
1,3-benzodioxol-4-yl N-methylcarbamate, melting point 146°–148° C.
7-chloro-2,2-dimethyl-1,3-benzodioxol-4-yl N-methylcarbamate, melting point 147°–148° C.
7-ethyl-2,2-dimethyl-1,3-benzodioxol-4-yl N-methylcarbamate, melting point 113°–115° C.

EXAMPLES 12–14

A stirred solution of 50 parts of phosgene in 200 parts of benzene was treated over one hour with a solution of 4-hydroxy-2,2-dimethyl-1,3-benzodioxole (33 parts) and dimethylaniline (24 parts) in benzene (150 parts) and stirred for a further 2 hours. The solution was then filtered, washed with water, dried and the 2,2-dimethyl-1,3-benzodioxol-4-yl chloroformate (41 parts, boiling point 83°–84° C/0.5 mm.) distilled off.

To a cold stirred solution of sodium carbonate (9.5 parts) and propargylamine hydrochloride (8.2 parts) in water (50 parts) and ether (40 parts) was added a solution of the chloroformate (16 parts) in either (40 parts). After stirring for one hour, the ethereal solution was washed, dried and evaporated to give 14.9 parts of 2,2-dimethyl-1,3-benzodioxol-4-yl N-propargylcarbamate, melting point 107°–109° C.

In a similar way by reacting the chloroformate with allylamine and dimethylamine respectively, the following compounds were prepared:

2,2-dimethyl-1,3-benzodioxol-4-yl N-allylcarbamate, melting point 93°–95° C.
2,2-dimethyl-1,3-benzodioxol-4-yl N,N-dimethylcarbamate, boiling point 119°–122° C at 0.5 mm. Hg. pressure.

EXAMPLE 15

EXAMPLE A

A solution of pyrogallol (50 parts) in ethyl methyl ketone (200 parts) was stirred and heated to 50° C, then phosphorus pentoxide was added portionwise at such a rate that the temperature remained about 80° C. After stirring for a further 30 minutes at about 50° C the liquid layer was poured into cold water (1,000 parts) and the crude product isolated by extracting with benzene and evaporating the extracts. Distillation of the crude product gave pure 4-hydroxy-2-ethyl-2-methyl-1,3-benzodioxole (39.5 parts), boiling point 84°–85° C/0.4 mm., melting point 48°–50° C.

EXAMPLE B

A solution of pyrogallol (63 parts) in 2,2-dimethoxypropane (100 parts) and benzene (100 parts) containing toluenesulphonic acid (0.01 parts) was slowly distilled through a fractionating column during 4 hours, removing liquid (150 parts), boiling point 57°–64° C. A few drops of triethylamine were then added and the mixture thoroughly washed with water, dried and evaporated. Distillation gave 4-hydroxy-2,2-dimethyl-1,3-benzodioxole (36 parts), boiling point 110° C/0.7 mm., which was purified by recrystallisation from carbon tetrachloride. Melting point 88°–90° C.

EXAMPLE 16

In a similar way to Example 15 the following compounds were prepared:

4-hydroxy-2,2-diethyl-1,3-benzodioxole, melting point 56°–58° C.
4-hydroxy-2,2-pentamethylene-1,3-benzodioxole, boiling point 130°–134° C at 0.3 mm. Hg. Pressure.
4-hydroxy-2,2-tetramethylene-1,3-benzodioxole, melting point 59°–62° C.
4-hydroxy-2-tertiarybutyl-2-methyl-1,3-benzodioxole, melting point 79°–81° C.

EXAMPLE 17

2,2-Dimethyl-1,3-benzodioxol-4-yl N-methylcarbamate (prepared as in Example 1) (8 parts) was refluxed for 15 minutes in acetic anhydride (40 parts) with a few drops of concentrated sulphuric acid. Sodium acetate (1 part) was added and most of the acetic anhydride was distilled off under vacuum. The remaining oil was poured into water (200 parts) and after standing for 1 hour was extracted into ether three times. The ether solution was washed with aqueous sodium bicarbonate solution and with water, then dried over sodium sulphate. The ether was distilled off under reduced pressure to yield 2,2-dimethyl-1,3-benzodioxol-4-yl N-acetyl-N-methylcarbamate, which was recrystallised from petroleum as a yellow crystalline solid, melting point 76°–77° C. (5.5 parts, 58% yield).

Analysis: Found: C, 59.10; H, 5.90; N, 5.05. $C_{13}H_{15}NO_5$ requires: C, 58.86; H, 5.70; N, 5.28%.

EXAMPLES 18 AND 19

The process of Example 17 was repeated replacing the carbamate starting material successively by 2,2-dimethyl-1,3-benzodioxol-4-yl N-propargyl carbamate and 2-ethyl-2-methyl-1,3-benzodioxol-4-yl N-methylcarbamate giving 2,2-dimethyl-1,3-benzodioxol-4-yl N-acetyl-N-propargyl carbamate, boiling point 138°–140° C/0.5 mm. Hg. pressure and 2-ethyl-2-methyl-1,3-benzodioxol-4-yl N-acetyl-N-methylcarbamate, boiling point 124°–126° C/0.4 mm. Hg. pressure.

EXAMPLE 20

A solution of 1,3-benzodioxol-4-yl methylcarbamate (100 parts) in acetic anhydride (350 parts) containing concentrated sulphuric acid (0.1 part) was boiled under reflux for 15 minutes. Anhydrous soldium acetate (50 parts) was then added and the excess of acetic anhydride distilled off under a reduced pressure of 25 mm mercury. The residue was diluted with benzene, filtered to remove solids, and the filtrate fractionally distilled to give 1,3-benzodioxol-4-yl N-acetyl-N-methylcarbamate (88 parts, 72% yield), boiling point 130° C/0.5 mm, melting point 48°–50° C.

Analysis: Found: C, 55.90; H, 4.60; N, 5.65%. $C_{11}H_{11}NO_5$ requires: C, 55.69; H, 4.67; N, 5.91%.

EXAMPLES 21–31

Following the process described in Example 20, the following compounds were prepared:

2-methyl-1,3-benzodioxol-4-yl N-acetyl-N-methylcarbamate, melting point 45° C.

2,2-diethyl-1,3-benzodioxol-4-yl N-acetyl-N-methylcarbamate, boiling point 138°-140° C at 0.5 mm. Hg. pressure.

2-methyl-2-t-butyl-1,3-benzodioxol-4-yl N-acetyl-N-methylcarbamate, boiling point 138° C at 0.5 mm. Hg. pressure.

1,3-benzodioxol-4-yl N-butyryl-N-methylcarbamate, boiling point 143° C at 0.5 mm. Hg. pressure.

2,2-dimethyl-1,3-benzodioxol-4-yl N-propionyl-N-methylcarbamate, boiling point 123° C at 0.1 mm. Hg. pressure.

2,2-dimethyl-1,3-benzodioxol-4-yl N-butyryl-N-methylcarbamate, boiling point 134°-140° C at 0.4 mm. Hg. pressure.

2,2-dimethyl-1,3-benzodioxol-4-yl N-pentanoyl-N-methylcarbamate, boiling point 137° C at 0.3 mm. Hg. pressure.

2,2,6-trimethyl-1,3-benzodioxol-4-yl N-acetyl-N-methylcarbamate, boiling point 140° C at 0.3 mm. Hg. pressure.

2,2-tetramethylene-1,3-benzodioxol-4-yl N-acetyl-N-methylcarbamate, boiling point 148° C at 0.5 mm. Hg. pressure.

2,2-pentamethylene-1,3-benzodioxol-4-yl N-acetyl-N-methylcarbamate, boiling point 153° C at 0.2 mm. Hg. pressure.

2,2-dimethyl-1,3-benzodioxol-4-yl N-acetyl-N-allylcarbamate, boiling point 136° C at 0.5 mm. Hg. pressure.

EXAMPLES 32 – 40

9 centimeter diameter filter papers treated with aqueous acetone solutions of each of the compounds 2,2-dimethyl-1,3-benzodioxol-4-yl N-methylcarbamate;
2,2-dimethyl-1,3-benzodioxol-4-yl N-acetyl-N-methylcarbamate;
1,3-benzodioxol-4-yl N-methylcarbamate;
1,3-benzodioxol-4-yl N-acetyl-N-methylcarbamate;
2-methyl-1,3-benzodioxol-4-yl N-acetyl-N-methylcarbamate;
1,3-benzodioxol-4-yl N-butyryl-N-methylcarbamate;
2,2-dimethyl-1,3-benzodioxol-4-yl N-butyryl-N-methylcarbamate;
2,2,6-trimethyl-1,3-benzodioxol-4-yl N-acetyl-N-methylcarbamate; and
2,2-dimethyl-1,3-benzodioxol-4-yl N-acetyl-N-allylcarbamate at rates equivalent to 100 milligrams per square foot (100 mgm./0.09 m².) of active ingredient were placed in 9 centimeter diameter Petri dishes. Batches of adult female houseflies (Musca domestica) lightly anaesthetised with carbon dioxide were then introduced into the dishes and a glass lid placed over each. After 24 hours the flies were examined and were all found to be dead.

EXAMPLES 41 – 48

7 centimeter diameter circular discs of cabbage leaves were painted with 1 milliliter aqueous acetone solutions of each of the following compounds:

2,2-dimethyl-1,3-benzodioxol-4-yl N-methylcarbamate,
2,2-dimethyl-1,3-benzodioxol-4-yl N-acetyl-N-methylcarbamate,
2,2,7-trimethyl-1,3-benzodioxol-4-yl N-methylcarbamate,
2,2-dimethyl-1,3-benzodioxol-4-yl N-allylcarbamate,
2,2-dimethyl-1,3-benzodioxol-4-yl N-propargylcarbamate,
2,2-dimethyl-1,3-benzodioxol-4-yl N-acetyl-N-propargylcarbamate,
2-ethyl-2-methyl-1,3-benzodioxol-4-yl N-methylcarbamate and
2,2-tetramethylene-1,3-benzodioxol-4-yl N-methylcarbamate, in each case at concentrations equivalent to leaf applications of 10, 5, 1, 0.5 and 0.25 pounds per acre (11.2, 5.6, 1.12, 0.56 and 0.28 kg./hectare) of active ingredient. When the deposit on the leaf discs had dried, each leaf disc was placed in a 9 centimeter diameter Petri dish, infested with ten second instar larvae of the cabbage white butterfly (*Pieris brassicae*) and covered with a glass lid. Three replications were made with each compound at each concentration level. After 48 hours the larvae were examined and were all found to be dead.

EXAMPLES 49 and 50

Aqueous suspensions containing 100 parts per million of 2,2-dimethyl-1,3-benzodioxol-4-yl N-methylcarbamate and 2,2-dimethyl-1,3-benzodioxol-4-yl N-acetyl-N-methylcarbamate were sprayed at a rate equivalent to 50 gallons per acre (585 liters per hectare) on young field beans (*Vicia faba*) infested with adult apterous vetch aphids (*Megoura viciae*). After treatment the plants were enclosed in glass cages with gauze tops for ventilation. Each treatment produced complete kill of the aphids in 24 hours as compared with no kill on control plants.

EXAMPLE 51

A wettable powder formulation was made by micronising the following:

2,2-dimethyl-1,3-benzodioxol-4-yl N-methylcarbamate: 25%
Hoe S1/263 (sodium salt of sulphonated condensation product of a long chain alcohol with ethylene oxide): 3%
China Clay: 72%

This was suitable for dispersion in water and spraying on plants.

EXAMPLE 52

A 5% granular formulation was made up as follows: Limestone grit and 2% Carbowax were tumbled for 30 minutes. 5% Finely ground 2,2-dimethyl-1,3-benzodioxol-4-yl N-methylcarbamate was then added and tumbled for 15 minutes. 1.25% of Calflo E (a proprietary calcium silicate) was then added and tumbled for a further 75 minutes to prevent sticking of the granules. The granules were finally sieved through a 12-mesh sieve.

EXAMPLE 53-60

Cylindrical pads of cotton wool, approximate diameter 1 cm., length 2 cms. were treated with ½ ml. of acetone solutions of the following carbamates:

2,2-dimethyl-1,3-benzodioxol-4-yl N-methylcarbamate,
2-methyl-1,3-benzodioxol-4-yl N-methylcarbamate,
2,2,7-trimethyl-1,3-benzodioxol-4-yl N-methylcarbamate, 2,2,6-trimethyl-1,3-benzodioxol-4-yl N-methylcarbamate, 2-ethyl-2-methyl-1,3-benzodioxol-4-yl N-methylcarbamate, 2,2-diethyl-1,3-benzodioxol-4-yl N-methylcarbamate, 2-tert-butyl-2-methyl-1,3-benzodioxol-4-yl N-methylcarbamate, 7-ethyl-2,2-dimethyl-1,3-benzodioxol-4-yl N-methylcarbamate, After leaving for 12 hours to dry, the pads were treated with 1 ml. of sheep blood serum and infested with 20 first instar larvae of the sheep blowfly (*Lucilia sericata*). After 24 hours, the blowflies were examined and found to be all dead; insects similarly infested on untreated pads were unaffected.

EXAMPLES 61-64

Acetone solutions of the compounds 2-methyl-2-t-butyl-1,3-benzodioxol-4-yl N-acetyl-N-methylcarbamate;

2,2-diethyl-1,3-benzodioxol-4-yl N-acetyl-N-methylcarbamate;

2,2-tetramethylene-1,3-benzodioxol-4-yl N-acetyl-N-methylcarbamate; and 2,2-pentamethylene-1,3-benzodioxol-4-yl N-acetyl-N-methylcarbamate were applied to the inside walls of glass tubes 9 cm high by 4.5 cm diameter so that after the acetone had evaporated a coating equivalent to 3 mg of active ingredient per square foot remained. Batches of adult female yellow fever mosquitos (*Aedes aegypti*) were then caged in the tubes. After 24 hours the mosquitos were examined and all found to be dead.

EXAMPLE 65

Filter papers, diameter 9 cm., were treated with 1 ml. of acetone solutions containing 30 parts per million of 2,2-dimethyl-1,3-benzodioxol-4-yl N-methylcarbamate or 7-chloro-2,2-dimethyl-1,3-benzodioxol-4-yl N-methylcarbamate. When they had dried, they were folded into quadrant shaped packets, infested with 20 first stage larvae of the cattle tick, *Boophilus microplus*, closed with a metal clip and kept at 25° C for 24 hours. At the end of this period it was found that all the ticks in the treated filter papers were dead, compared with fewer than 5% of those in control experiments.

EXAMPLE 66

2,2-Dimethyl-1,3-benzodioxol-4-yl N-butyroyl-N-methylcarbamate 2,2-Dimethyl-1,3-benzodioxol-4-yl methylcarbamate (8g) was heated at 150° C in n-butyric anhydride (40 ml) in the presence of sulphuric acid (3 drops) for 25 minutes. Sodium-n-butyrate (0.5g) was added and the excess anhydride distilled off under vacuum. Treatment with water and isolation through ether extraction gave an oil which was distilled. The yield was 6g (60%), bp 134°-40° C/0.4 mm.

Analysis: Found: C, 61.60; H, 6.50; N, 4.45%. $C_{15}H_{19}NO_5$ requires: C, 61.42; H, 6.53; N, 4.78%.

EXAMPLE 67

2,2-Dimethyl-1,3-benzodioxol-4-yl N-methyl-N-propionylcarbamate 2,2-Dimethyl-1,3-benzodioxol-4-yl methylcarbamate (9g) was boiled under reflux in propionic anhydride (25 ml) in the presence of sulphuric acid (5 drops) for 25 minutes. Sodium acetate (0.5g) was added and the excess propionic anhydride distilled off under vacuum. Treatment with water and isolation through ether extraction gave a viscous oil which was distilled. The yield was 4.5g (40%), bp 130°-45° C/0.01 mm.

Analysis: Found: C, 60.25; H, 6.40; N, 4.60%. $C_{14}H_{17}NO_5$ requires: C, 60.20; H, 6.14; N, 5.02%.

EXAMPLE 68

2,2-Dimethyl-1,3-benzodioxol-1,3-benzodioxol-4-yl N-methyl-N-yaleroylcarbamate 2,2-Dimethyl-1,3-benzodioxol-4-yl methylcarbamate (9g) was heated at 150° C in valeric anhydride (25 ml) in the presence of sulphuric acid (5 drops) for 25 minutes. Sodium acetate (0.5g) was added and the excess valeric anhydride removed under vacuum. Addition of water and isolation through ether extraction gave a viscous oil which was distilled. The yield was 6.5g (51%), bp. 135°-48° C/0.3 mm.

Analysis: Found: C, 62.75; H, 7.20; N, 4.30%. $C_{16}H_{21}NO_5$ requires: C, 62.52; H, 6.89; N, 4.56%.

1,3-Benzodioxol-4-yl N-acetyl-N-methylcarbamate (compound 1), 2,2-dimethyl-1,3-benzodioxol-4-yl N-propionyl-N-methylcarbamate (compound 2), 2,2-dimethyl-1,3-benzodioxol-4-yl N-butyryl-N-methylcarbamate (compound 3), 2,2-dimethyl-1,3-benzodioxol-4-yl N-pentanoyl-N-methylcarbamate (compound 4), 2,2-dimethyl-1,3-benzodioxol-4-yl N-methylcarbamate (compound 5) and 2,2-dimethyl-1,3-benzodioxol-4-yl N-acetyl-N-methylcarbamate (compound 6) were further tested as described in the following Examples 69-76.

EXAMPLE 69

Compounds 2 and 4 and also 2,2-dimethyl-1,3- benzodioxol-4-yl N-methylcarbamate(compound 5) and 2,2-dimethyl-1,3-benzodioxol-4-yl N-acetyl-N-methylcarbamate (compound 6) were tested for activity against the 2nd stage nymph of the German cockroach (*Blattella germanica*), of the order *Orthoptera*, by treating the walls of glass tubes (9.0 cm high × 4.5 cm diameter) with acetone solutions of the compounds and after the acetone had evaporated caging the insects in the tubes for 48 hours. The highest dosage rate employed was 50 mg/ft²(532 mg/m²).

If complete kill was obtained at the highest dosage rate, the test was repeated using a logarithmically reducing dose regime until less than 50% mortality was recorded. The LC50 was then calculated from the line of best fit from the data plotted on log/provit analysis paper.

The LC50 values are abbreviated on a 0-6 scale where

| | |
|---|---|
| 0 = >50 mg/ft² (>532 mg/m²) | 4 = 0.5-1.5 mg/ft² (5.3-16 mg/m²) |
| 1 = 15-50 mg/ft² (160-532 mg/m²) | 5 = 0.15-0.5 mg/ft² (1.6-5.3 mg/m²) |
| 2 = 5-15 mg/ft² (53-160 mg/m²) | 6 = <0.5 mg/ft²(<5.3 mg/m²) |
| 3 = 1.5-5 mg/ft² (16-53 mg/m²) | |

Results are as follows:

| Compound No. | LC50 value | Compound No | LC50 value |
| --- | --- | --- | --- |
| 2 | 6 | 5 | 5 |
| 4 | 5 | 6 | 1 |

Similarly LC50 values were obtained against various pests as described in Examples 70–73 where, however, the LC50 values are abbreviated on a 0–6 scale where

| | | |
| --- | --- | --- |
| 0 = >1000 parts per million (ppm) | or | >1000 mg/ft$^2$ (10.65 g/m$^2$) |
| 1 = 300 – 1000 ppm | or | 300–1000 mg/ft$^2$ (3.20 – 10.65 g/m$^2$) |
| 2 = 100 – 299 ppm | or | 100–299 mg/ft$^2$ (1.07 – 3.19 g/m$^2$) |
| 3 = 30 – 99 ppm | or | 30–99 mg/ft$^2$ (0.32 – 1.06 g/m$^2$) |
| 4 = 10 – 29 ppm | or | 10–29 mg/ft$^2$ (107–310 mg/m$^2$) |
| 5 = 3 – 9 ppm | or | 3–9 mg/ft$^2$ (32–106 mg/m$^2$) |
| 6 = <3 ppm | or | <3 mg/ft$^2$ (<32 mg/m$^2$) |

EXAMPLE 70

LC50 values were obtained for each of Compounds 1, 2, 3, 4, 5 and 6 against adult female houseflies (*Musca domestica*), of the order Diptera. The tests were carried out by adding acetone solutions of the compounds to 9 cm diameter filter papers in the base of 9 cm diameter crystallising dishes, placing the houseflies in the dishes after the acetone had evaporated, closing the dishes with Petri dish lids and counting the mortality after 24 hours. The highest dosage rate employed was 1000 mg/ft$^2$ (10.65 g/m$^2$).

Results are as follows:

| Compound No | LC50 value |
| --- | --- |
| 1 | 5 |
| 2 | 5 |
| 3 | 4 |
| 4 | 4 |
| 5 | 4 |
| 6 | 3 |

EXAMPLE 71

Similarly, LC50 values were obtained for each of Compounds 1, 2, 3, 4, 5 and 6 against larvae of the sheep maggot fly (*Lucilia sericata*), of the order Diptera. The tests were carried out by placing newly hatched larvae on dental rolls contained in glass vials and soaked with 1 ml of blood serum containing the compound. The mortality was assessed after 24 hours. The highest dosage rate employed was 1000 ppm.

Results are:

| Compound No | LC50 value |
| --- | --- |
| 1 | 3 |
| 2 | 5 |
| 3 | 5 |
| 4 | 3 |
| 5 | 5 |
| 6 | 3 |

EXAMPLE 72

Similarly, LC50 values were obtained for each of Compounds 2 and 4 against larvae of the cattle tick (*Boophilus microplus*), of the order Acarina. The tests were carried out evaporating 1 ml of an acetone solution of the compound on 9 cm diameter filter papers, folding the papers twice in half after drying to give quadrant shaped packets and sealing the tick larvae therein for 24 hours by means of a paper clip. The highest dosage rate employed was 1000 ppm.

Results are:

| Compound No | LC50 value |
| --- | --- |
| 2 | 5 |
| 4 | 3 |

EXAMPLE 73

Similarly, LC50 values were obtained for each of Compounds 1, 2, 4, 5 and 6 against adult red spider mites (*Tetranychus telarius*), of the order Acarina. The tests were carried out by spraying infected French beans with a 50% acetone water solution of the compound, containing 500 ppm of Lissapol NX as a wetting agent, and recording the mortality after 48 hours. The highest dosage rate employed was 1000 ppm which is equivalent to 10 lb/acre (11.20 kg/ha).

Results are:

| Compound No. | LC50 value |
| --- | --- |
| 1 | 2 |
| 2 | 1 |
| 4 | 1 |
| 5 | 0 |
| 6 | 2 |

EXAMPLE 74

Persistency was measured against German cockroaches (*Blattella germanica*), or the order Orthoptera, by treating glass plates with acetone solutions of the compunds listed below to produce a deposit equivalent to 100 mg/ft$^2$ (1.065 g/m$^2$), and caging 2nd stage nymph cockroaches on these surfaces for 48 hours at 7 day intervals until less than 50% mortality was recorded.

Results in days are:
Compound 2 : 21 – 28
Compound 4 : > 35
Compound 6 : 8 – 14

EXAMPLE 75

Persistency was measured against yellow fever mosquito (*Aedes aegypti*), of the order Diptera, by treating glass plates with acetone solutions of the compounds listed below to produce a deposit equivalent to 100 mg/ft$^2$ (1.065 g/m$^2$), and caging adult female mosquitos on these surfaces for 24 hours at 7 day intervals until less than 50% mortality was recorded.

Results in days are:
Compound 1 : 35
Compound 6 : 15 – 21

EXAMPLE 76

Mammalian toxicity was assessed by measuring the acute oral LD50 to rats and mice. Componds were dissolved or suspended in a 0.4% tragacanth solution and administered by stomach tube to the test animal.

The mice used were 10 to 15 g weanlings of the Carshalton CFW strain whilst the rats were 30 to 40 g weanlings of Wystar strain. Three replicates per dosage rate were employed and the mortality was recorded daily for up to 5 days. The LD50 values were calculated as for those for insecticidal and acaricidal activity above. Results are as follows:

| Compound No. | Species | Acute oral LD50 values in mg/kg body wt. | | |
|---|---|---|---|---|
| | | rat male | rat female | mouse |
| 1 | | >1000 | >1000 | >4000 |
| 2 | | — | — | 280 |
| 3 | | >1000 | >1000 | 2000 |
| 4 | | — | — | 170 |
| 5 | | 45 | — | 45 |

The intermediate hydroxy benzodioxoles of the formula:

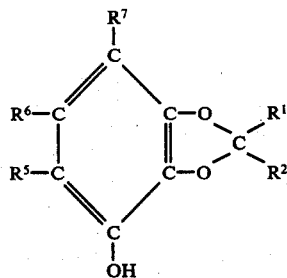

wherein $R^1$, $R^2$, $R^5$, $R^6$ and $R^7$ are as defined above, excluding the cases where $R^1$ and $R^2$ are hydrogen or methyl when $R^5$, $R^6$ and $R^7$ are all hydrogen, are new compounds and are embraced within the present invention. These compounds are suitably prepared from 1,2,3-trihydroxybenzene (pyrogallol) by reaction with the appropriate keytone in the presence of phosphorus pentoxide using the ketone as solvent.

We claim:

1. A pesticidal composition for combating insects and acarids comprising a pesticidal amount of a compound of the formula

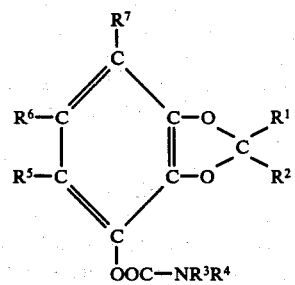

wherein
$R^1$ and $R^2$ are selected from the group consisting of hydrogen and alkyl of 1 to 6 carbon atoms and a group where $R^1$ and $R^2$ together with the linking carbon atom form a cycloaliphatic ring selected from the group consisting of cycloalkane and cycloalkene rings of 5 to 7 carbon atoms;
$R^3$ is selected from the group consisting of hydrogen, alkyl of 1 to 4 carbon atoms and lower alkanoyl;
$R^4$ is selected from the group consisting of alkyl of 1 to 4 carbon atoms, alkenyl of up to 4 carbon atoms and alkynyl of up to 4 carbon atoms; and
one of $R^5$, $R^6$ and $R^7$ are selected from the group consisting of hydrogen, halogen and alkyl of 1 to 4 carbon atoms, and wherein the remaining members of $R^5$, $R^6$ and $R^7$ each represent hydrogen in combination with at least one material selected from the group consisting of carriers, wetting agents, and mixtures thereof.

2. A pesticidal composition as in claim 1 which contains a wetting agent.

3. A pesticidal composition as in claim 1, which contains at least one other active material selected from the group consisting of insecticides, bactericides and fungicides.

4. A pesticidal composition as claimed in claim 1 wherein $R^3$ is selected from the group consisting of hydrogen, alkyl of 1 to 5 carbon atoms, acetyl and propionyl.

5. A pesticidal composition as claimed in claim 1 wherein $R^3$ represents a hydrogen atom and $R^4$ represents a methyl group.

6. A pesticidal composition as claimed in claim 1, wherein $R^5$, $R^6$ and $R^7$ each represent a hydrogen atom.

7. A pesticidal composition according to claim 1, wherein the pesticidal compound is a compound of the formula:

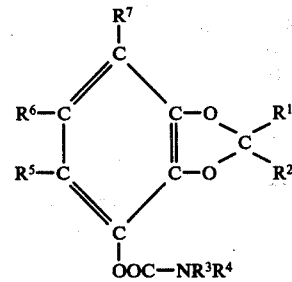

wherein
$R^1$ and $R^2$ are selected from the group consisting of hydrogen and alkyl of 1 to 6 carbon atoms and a group where $R^1$ and $R^2$ together with the linking carbon atom form a cycloalkane ring of 5 to 7 carbon atoms;
$R^3$ is selected from the group consisting of hydrogen, alkyl of 1 to 4 carbon atoms and lower alkanoyl;
$R^4$ is selected from the group consisting of alkyl of up to 4 carbon atoms, alkenyl of up to 4 carbon atoms and alkynyl of up to 4 carbon atoms; and
one of $R^5$, $R^6$ and $R^7$ is selected from the group consisting of hydrogen, halogen and alkyl of 1 to 4 carbon atoms; and
the others of $R^5$, $R^6$ and $R^7$ each represent a hydrogen atom.

8. A pesticidal composition as claimed in claim 7 wherein one of $R^5$, $R^6$ and $R^7$ is selected from the group consisting of hydrogen and alkyl of 1 to 4 carbon atoms and the others of $R^5$, $R^6$ and $R^7$ each represent a hydrogen atom.

9. A pesticidal composition as claimed in claim 7 wherein $R^1$ and $R^2$ each represent a methyl group.

10. A pesticidal composition as claimed in claim 7 wherein $R^3$ represents a hydrogen atom and $R^4$ represents a methyl group.

11. A pesticidal composition as claimed in claim 7 wherein $R^5$, $R^6$ and $R^7$ each represent a hydrogen atom.

12. A pesticidal composition as claimed in claim 7 wherein the pesticidal compound is 1,3-benzodioxol-4-yl N-acetyl-N-methylcarbamate.

13. A pesticidal composition as claimed in claim 7 wherein the pesticidal compound is 2,2-dimethyl-1,3-benzodioxol-4-yl N-propionyl-N-methylcarbamate.

14. A pesticidal composition as claimed in claim 7 wherein the pesticidal compound is 2,2-dimethyl-1,3-benzodioxol-4-yl N-butyryl-N-methylcarbamate.

15. A pesticidal composition as claimed in claim 7 wherein the pesticidal compound is 2,2-dimethyl-1,3-benzodioxol-4-yl N-pentanoyl-N-methylcarbamate.

16. A pesticidal composition as claimed in claim 7, wherein the pesticidal compound is 2,2-dimethyl-1,3-benzodioxol-4-yl N-methylcarbamate.

17. A pesticidal composition as in claim 16, which further contains a wetting agent.

18. A pesticidal composition as in claim 17, wherein the wetting agent is selected from the group consisting of organic anionic, nonionic and cationic wetting agents.

19. A pesticidal composition as in claim 7, wherein the pesticidal compound is 2,2-dimethyl-1,3-benzodioxole-4-yl N,N-dimethylcarbamate.

20. A pesticidal composition as claimed in claim 7, wherein the pesticidal compound is 2,2,7-trimethyl-1,3-benzodioxol-4-yl N-methylcarbamate.

21. A pesticidal composition according to claim 1, wherein the carrier is a solvent.

22. A pesticidal composition according to claim 1, wherein the carrier is a solid inert diluent.

23. A method of combating insect and acarid pests which comprises applying to a locus a pest-combating amount of a compound of the formula $$\begin{array}{c} R^7 \\ | \\ C \\ \diagup \diagdown \\ R^6-C \quad\quad C-O \quad R^1 \\ \| \quad\quad\quad\quad \diagdown C \diagup \\ R^5-C \quad\quad C-O \quad R^2 \\ \diagdown \diagup \\ C \\ | \\ OOC-NR^3R^4 \end{array}$$

wherein
R$^1$ and R$^2$ are selected from the group consisting of hydrogen and alkyl of 1 to 6 carbon atoms and a group where R$^1$ and R$^2$ together with the linking carbon atom form a cycloaliphatic ring selected from the group consisting of cycloalkane and cycloalkene rings of 5 to 7 carbon atoms;
R$^3$ is selected from the group consisting of hydrogen, alkyl of 1 to 4 carbon atoms and lower alkanoyl;
R$^4$ is selected from the group consisting of alkyl of 1 to 4 carbon atoms, alkenyl of up to 4 carbon atoms and alkynyl of up to 4 carbon atoms; and one of R$^5$, R$^6$ and R$^7$ are selected from the group consisting of hydrogen, halogen and alkyl of 1 to 4 carbon atoms, and wherein the remaining members of R$^5$, R$^6$ and R$^7$ each represent hydrogen.

24. A method according to claim 23, wherein the pests are insects.

25. A method as in claim 23, wherein the pesticidal compound is a compound of the formula:

$$\begin{array}{c} R^7 \\ | \\ C \\ \diagup \diagdown \\ R^6-C \quad\quad C-O \quad R^1 \\ \| \quad\quad\quad\quad \diagdown C \diagup \\ R^5-C \quad\quad C-O \quad R^2 \\ \diagdown \diagup \\ C \\ | \\ OOC-NR^3R^4 \end{array}$$

wherein
R$^1$ and R$^2$ are selected from the group consisting of hydrogen and alkyl of 1 to 6 carbon atoms and a group where R$^1$ and R$^2$ together with the linking carbon atom form a cycloalkane ring of 5 to 7 carbon atoms;
R$^3$ is selected from the group consisting of hydrogen, alkyl of 1 to 4 carbon atoms and lower alkanoyl;
R$^4$ is selected from the group consisting of alkyl of up to 4 carbon atoms, alkenyl of up to 4 carbon atoms and alkynyl of up to 4 carbon atoms; and
one of R$^5$, R$^6$ and R$^7$ is selected from the group consisting of hydrogen, halogen and alkyl of 1 to 4 carbon atoms; and
the others of R$^5$, R$^6$ and R$^7$ each represent a hydrogen atom.

26. A method as in claim 25, wherein one of R$^5$, R$^6$ and R$^7$ is selected from the group consisting of hydrogen and alkyl of 1 to 4 carbon atoms and the others of R$^5$, R$^6$ and R$^7$ each represent a hydrogen atom.

27. A method as in claim 25, wherein R$^1$ and R$^2$ each represent a methyl group.

28. A method as in claim 25, wherein R$^3$ represents a hydrogen atom and R$^4$ represents a methyl group.

29. A method as in claim 25, wherein R$^5$, R$^6$ and R$^7$ each represent a hydrogen atom.

30. A method as in claim 25, wherein the pesticidal compound is 2,2dimethyl-1,3-benzodioxol-4-yl N-methylcarbamate.

31. A method as in claim 25, wherein the pesticidal compound is 2,2,7-trimethyl-1,3-benzodioxol-4-yl N-methylcarbamate.

32. A method according to claim 30, wherein the compound is used for combating insects in an insecticidal amount.

33. A method as in claim 25, wherein the pesticidal compound is 2,2-dimethyl-1,3-benzodioxole-4-yl N,N-dimethylcarbamate.

* * * * *